US007132522B1

(12) United States Patent
Becher et al.

(10) Patent No.: US 7,132,522 B1
(45) Date of Patent: Nov. 7, 2006

(54) REGULATORY SEQUENCES AND EXPRESSION CASSETTES FOR YEASTS, ESPECIALLY FOR KLUYVEROMYCES

(75) Inventors: Dietmar Becher, Diedrichshagen (DE); Rimantas Siekstele, Vilnius (LT); Danguole Bartkeviciute, Vilnius (LT); Kestutis Sasnauskas, Vilnius (LT); Leopold Döhner, Greifswald (DE); Salah Salim, Kiel (DE)

(73) Assignee: TAD Pharma GmbH, Cuxhaven (DE)

( * ) Notice: Subject to any disclaimer, the term of this patent is extended or adjusted under 35 U.S.C. 154(b) by 0 days.

(21) Appl. No.: 10/070,574

(22) PCT Filed: Sep. 5, 2000

(86) PCT No.: PCT/EP00/08662

§ 371 (c)(1),
(2), (4) Date: Nov. 12, 2002

(87) PCT Pub. No.: WO01/20005

PCT Pub. Date: Mar. 22, 2001

(30) Foreign Application Priority Data

Sep. 10, 1999 (DE) ................................. 199 43 383

(51) Int. Cl.
| | | |
|---|---|---|
| C07H 21/02 | (2006.01) | |
| C07H 21/04 | (2006.01) | |
| C12N 15/00 | (2006.01) | |
| C12N 15/09 | (2006.01) | |
| C12N 15/63 | (2006.01) | |

(52) U.S. Cl. ................. 536/23.1; 536/24.1; 435/320.1; 435/69.1; 435/71.1; 435/252.3

(58) Field of Classification Search ............... 536/23.1, 536/24.1; 435/320.1, 69.1, 71.1, 252.33
See application file for complete search history.

(56) References Cited

U.S. PATENT DOCUMENTS 4,859,596 A    8/1989   Hollenberg et al.
4,943,529 A    7/1990   Van den Berg et al.

OTHER PUBLICATIONS

Siekstele et al. Cloning, Targeted Disruption and Heterologous Expression of the *Kluyveromyces marxianus* Endopolygalcturonase Gene (EPG1) Yeast vol. 15 No. 4 Mar. 15, 1999 pp. 311-322.*
Accession No. AF000076, Mar. 17, 1999.*
Bartkeviciute et al. Construction of Stable Autonomously Replicating Vector for Yeast *Kluyveromyces*. *Biologija* 2:22-23 (1996).
Bird et al. The tomato polygalacturonase gene and ripening-specific expression in transgenic plants. *Plant Molecular Biology II* 11:651-662 (1998).
Bussink et al. Characterization of polygalacturonase-overproducing *Aspergilus niger* transformants. *Appl. Microbiol. Biotechnol.* 37:324-329 (1992).
Nicholass et al. High levels of ripening-specific reporter gene expression directed by tomato fruit polygalacturonase gene-flanking regions. *Plant Molecular Biology* 28:423-435 (1995).
Siekstele et al. Cloning, Targeted Disruption and Heterologous Expression of the *Kluyveromyces marxianus* Endopolygalacturonase Gene (EPG1). *Yeast* 15:311-322 (1999).

* cited by examiner

*Primary Examiner*—James Ketter
*Assistant Examiner*—Konstantina Katcheves
(74) *Attorney, Agent, or Firm*—Needle & Rosenberg, P.C.

(57) ABSTRACT

The invention relates to a DNA sequence which acts as a promoter in yeast cells, to an expression and optionally, secretion system containing said DNA sequence, to plasmids containing this system, to host cells that have been transformed with said DNA and to methods for producing proteins and polypeptides.

22 Claims, 7 Drawing Sheets

Fig.1 pEPG1-2

-32 cacagattaa gctcagaaaC(aaaaaaaaaa aa ATG... ORF EPG...

TAA gc gtctcttttt attttttttt tttttttt)Tat taacgtgaag aag

.......cacagattaa gctcagaaaCTTAAG Tat taacgtgaag aag......

↑
BspTI

Fig.5 rPEPG: 5'TTAACAGCTGTCTCTCTTTTCCAATGGAGAAGC 3'
PvuII vPEPG: 5'TTAAGAGGCCTGTCCGATTATAAACTTGCGGC 3'
StuI

SEQUENCE LISTING

```
<160> NUMBER OF SEQ ID NOS: 9

<210> SEQ ID NO 1
<211> LENGTH: 1146
<212> TYPE: DNA
<213> ORGANISM: Kluyveromyces marxianus

<400> SEQUENCE: 1
gaggcctgtc cgattattaa acttgcggca cccgagtttg tgaccttcga cgacatgttt      60
tatttccaca ccgtagctac actttctatg tagtaagtag gtagtatgga tggtagctag     120
tagaaactaa acgaaacgaa ataaatgtga aatgttagac gtaaagggga ggggaaggga     180 aggggcggc ggagagacat gccaagccat gccatttcat ggcatggcat gtcaagggat      240
actgcatgca tgcatgcata ctttaccaat agcaaagtaa attgctttct tcccccattt     300
gaaactattc cacctcaatc catctttttct ataatgggta tcaccgatct catgtgttct    360
```

```
aataatgctg caggcaacaa caaatcttaa aggcaacttg gaatgtaatt tggttaatga     420
tagatatcaa acagcaatgg tgggctccaa ccgcatggat atgctcacct tattatccgg     480
aattgttgtt ccgcaggaaa aaaaaaaaac ctcgaaccag atattaatta tcctatcatt     540
actgcgtaca aaacccggga acggttaacc tgcagcagcc gttttgctta cagttctcat     600
gcacaatcag ccagattttg caatagtatt aacttagaat taaggcaaca tctttggata     660
tgcatgtaga gtaagtcgtt cgaaaccatt attattatta ttattattat tattattatt     720
attattatta ttattagtat tattgaaatt gttattgttc ttagtttcac tactattatt     780
attcatattc atgttattga catcgccgaa cgaccagcct ccataccgat tagacaggat     840
ctcaaacgtg ggctccagag ctcacacatt atgctaaata actatctact gtaacagcta     900
cagaaaaaaa actataaaag agcgagggat aaaccactct cttgtgaatc aggatcagta     960
ggtaactcat aaaccttctt cttttctctc aaaatatcaa ataacagtag tatcaacaac    1020
gatatcgaat aatactaact actacaacag taggaacagt aacgacaacg acaacgatag    1080
taacgacaat aacgcacacca acaaacaaca ggaacacaga ttaagctcag aaacaaaaaa    1140
aaaaaa                                                               1146

<210> SEQ ID NO 2
<211> LENGTH: 541
<212> TYPE: DNA
<213> ORGANISM: Kluyveromyces marxianus

<400> SEQUENCE: 2
gcgtctcttt ttattttttt ttttttttt attaacgtga agaagataag ggaagtcttc      60
aatgcggttc tgaatggttg atccatttcg atacctcggg gacttccttt gaatatattc    120
tgagagtatg acagttggtt ttcttcttt ctttctattg ttttgtttt tatggaaata     180 tagctttgat gatttaggat attttttgta gtgaaccaat acatgcttga ttaatatacg    240
tacgaggtgg gcattctact ctcattattg gtgttttatt ggagggaaaa attaaatcta    300
ggagtatcgt ttagagcgcg aacgtaatat ccatgttctt ctctttgaag aggtcccacc    360
attgcttccc agatagccag cattcttcca tgatattttg cgcttgtttt gcactggtga    420 cacccttttcg aaccaaagat gtcaagtgct gctgatacaa caacctgtat tcatacaatt    480
ctggatccat cagctcacaa tccacagctg aagatacaga aaatgataca tgtctctgca    540
g                                                                    541

<210> SEQ ID NO 3
<211> LENGTH: 75
<212> TYPE: DNA
<213> ORGANISM: Kluyveromyces marxianus

<400> SEQUENCE: 3
atgttattca gcaacacctt attgatcgca gcagctagtg cattattagc tgaagcttct     60
ccattggaaa agaga                                                      75

<210> SEQ ID NO 4
<211> LENGTH: 33
<212> TYPE: DNA
<213> ORGANISM: Kluyveromyces marxianus

<400> SEQUENCE: 4
ttaacagctg tctctctttt ccaatggaga agc                                  33
```

-continued

```
<210> SEQ ID NO 5
<211> LENGTH: 32
<212> TYPE: DNA
<213> ORGANISM: Kluyveromyces marxianus

<400> SEQUENCE: 5
ttaagaggcc tgtccgatta taaacttgcg gc                                      32

<210> SEQ ID NO 6
<211> LENGTH: 30
<212> TYPE: DNA
<213> ORGANISM: Polyomavirus sp.

<400> SEQUENCE: 6
tcaagcttaa gaatggcccc aacaaaaaga                                         30

<210> SEQ ID NO 7
<211> LENGTH: 30
<212> TYPE: DNA
<213> ORGANISM: Polyomavirus sp.

<400> SEQUENCE: 7
gtaagcttaa gattacagca ttttttgtctg                                        30

<210> SEQ ID NO 8
<211> LENGTH: 32
<212> TYPE: DNA
<213> ORGANISM: Hepatitis B virus

<400> SEQUENCE: 8
agccttaaga taatggagaa catcacatca gg                                      32

<210> SEQ ID NO 9
<211> LENGTH: 27
<212> TYPE: DNA
<213> ORGANISM: Hepatitis B virus

<400> SEQUENCE: 9
tgacttaagt taaatgtata cccaaag                                            27
```

REGULATORY SEQUENCES AND EXPRESSION CASSETTES FOR YEASTS, ESPECIALLY FOR KLUYVEROMYCES

The invention concerns a DNA sequence which is active as a promoter in yeast cells, an expression and optionally secretion system containing the DNA sequence, plasmids containing that system, host cells that have been transformed with the DNA, and methods of producing proteins and polypeptides.

The production of peptides and proteins with gene-technology methods has become the usual practice in the meantime and many different systems are available for that purpose. Frequently, use is made of bacteria systems which however suffer from disadvantages, in particular in regard to producing medicaments or vaccines, for example that they produce pyrogenic substances which have to be removed prior to use, or they cannot glycosylate the polypeptides. Therefore, a series of other systems for the expression of polypeptides in eukaryotic cells have also been developed. An organism which is wide-spread for that purpose is the yeast *Saccharomyces cerevisiae*, the genome of which is known in the meantime and can be obtained for the vectors and expression systems. However the use of that microorganism also involves disadvantages. Thus *Saccharomyces* is for example temperature-sensitive, which requires expensive pieces of equipment for temperature control in culture.

A genus which is considered for bio-technological methods by virtue of advantageous properties is the yeast *Kluyveromyces*. The species *K. lactis* and *K. marxianus* are classified as GRAS (Generally Recognised As Save) and can therefore be used with the same security as *Saccharomyces*. In addition *K. marxianus* can use a large number of carbon sources and energy sources for growth and is not very temperature-sensitive. *Kluyveromyces marxianus* can grow at temperatures of up to 45° C. and can therefore be more easily cultured, in contrast to the temperature-sensitive *Saccharomyces* strains. The cells of rapidly growing *K. marxianus* strains can divide under optimum conditions every 35 minutes. However it was hitherto not possible to make optimum use of those good properties as reliable, strong-expression variable promoters are lacking for that type of yeast and there are scarcely any expression systems available, with which proteins can be produced with a high level of effectiveness.

Now, the object of the present invention was to provide a promoter which is suitable for expression in yeasts, in particular yeast cells of the genus *Kluyveromyces*, as well as expression systems which can be used variably for expression.

That object is attained in that in accordance with the invention a DNA sequence which includes the nucleotide sequence in accordance with SEQ ID No 1

```
GAGGCCTGTC CGATTATTAA ACTTGCGGCA CCCGAGTTTG
TGACCTTCGA CGACATGTTT TATTTCCACA CCGTAGCTAC
ACTTTCTATG TAGTAAGTAG GTAGTATGGA TGGTAGCTAG
TAGAAACTAA ACGAAACGAA ATAAATGTGA AATGTTAGAC
GTAAAGGGGA GGGGAAGGGA AGGGGCGGC GGAGAGACAT
GCCAGCCAT GCCATTTCAT GGCATGGCAT GTCAAGGGAT
ACTGCATGCA TGCATGCATA CTTTACCAAT AGCAAAGTAA
```

-continued
```
ATTGCTTTCT TCCCCCATTT GAAACTATTC CACCTCAATC
CATCTTTTCT ATAATGGGTA TCACCGATCT CATGTGTTCT
AATAATGCTG CAGGCAACAA CAAATCTTAA AGGCAACTTG
GAATGTAATT TGGTTAATGA TAGATATCAA ACAGCAATGG
TGGGCTCCAA CCGCATGGAT ATGCTCACCT TATTATCCGG
AATTGTTGTT CCGCAGGAAA AAAAAAAAC CTCGAACCAG
ATATTAATTA TCCTATCATT ACTGCGTACA AAACCCGGGA
ACGGTTAACC TGCAGCAGCC GTTTTGCTTA CAGTTCTCAT
GCACAATCAG CCAGATTTTG CAATAGTATT AACTTAGAAT
TAAGGCAACA TCTTTGGATA TGCATGTAGA GTAAGTCGTT
CGAAACCATT ATTATTATTA TTATTATTAT TATTATTATT
ATTATTATTA TTATTAGTAT TATTGAAATT GTTATTGTTC
TTAGTTTCAC TACTATTATT ATTCATATTC ATGTTATTGA
CATCGCCGAA CGACCAGCCT CCATACCGAT TAGACAGGAT
CTCAAACGTG GGCTCCAGAG CTCACACATT ATGCTAAATA
ACTATCTACT GTAACAGCTA CAGAAAAAAA ACTATAAAAG
AGCGAGGAT AAACCACTCT CTTGTGAATC AGGATCAGTA
GGTAACTCAT AAACCTTCTT CTTTTCTCTC AAAATATCAA
ATAACAGTAG TATCAACAAC GATATCGAAT AATACTAACT
ACTACAACAG TAGGAACAGT AACGACAACG ACAACGATAG
TAACGACAAT AACGACACCA ACAAACAACA GGAACACAGA
TTAAGCTCAG AAACAAAAAA AAAAAA
``` is provided.

The nucleotide sequence according to the invention includes a sequence which is active as a promoter and furnishes an expression system which is highly variable and suitable for *Kluyveromyces*, but can also be used for other types of yeast, in particular *Saccharomyces cerevisiae*.

The DNA sequence according to the invention, in accordance with SEQ ID No 1 is a nucleic acid sequence which contains regulatory regions of a gene which codes for the enzyme endopolygalacturonase. The enzyme endopolygalacturonase breaks down pectin insofar as it cleaves 1,4-α-D-galactosituronic bonds between two non-methylated galacturonic acid esters. That enzyme occurs inter alia in yeast strains of the type *Kluyveromyces marxianus*. The sequence of the endopolygalacturonase gene from *Kluyveromyces marxianus* var. *marxianus* was published in Yeast 15, 311–322 (1999). The promoter region which can be derived from the stated sequence however did not reliably result in the expression of various proteins.

It has now been found that a sequence which includes a part of the nucleotides of SEQ ID No 1, preferably at least the nucleotides 1 to 1134 and in particular the entire sequence permits the expression of proteins in a highly advantageous and reproducible fashion. The claimed sequence in accordance with SEQ ID No 1 has a plurality of regulatory components so that it can perform its function as a promoter under the most widely varying conditions. The promoter according to the invention can be induced by the addition of pectin to the culture medium. That is advantageous as pectin is a readily available substance and thus an advantageous induction agent is available for the system according to the invention.

The described nucleic acid sequences with a regulatory activity include such sequences which have occurred by virtue of modification, substitution, deletion or insertion or combinations thereof, which involve the same or better regulatory activity than the promoter, the terminator or the signal sequence. For that purpose it is also possible to include the sequence in accordance with SEQ ID No 1 with further regulatory upstream sequences with activator and/or repressor functions.

In accordance with the invention moreover such sequences are also considered, which with the claimed nucleotides or sequences have a homology of at least 80%, preferably at least 90% and in particular 95%, as long as they also have comparable activity.

Preferably the sequence in accordance with SEQ ID No 1 is afforded in the form of an expression system or an expression cassette for the expression of proteins and peptides. The expression cassette according to the invention includes in its simplest form a regulatory sequence as is shown in SEQ ID No 1 or a part thereof which is active as a promoter, an insertion cloning site into which the polynucleotide can be cloned for the protein to be expressed, and the nucleotide sequence in accordance with SEQ ID No 2

```
GCGTCTCT TTTTATTTTT TTTTTTTTTT TTATTAACGT

GAAGAAGATA AGGGAAGTCT TCAATGCGGT TCTGAATGGT

TGATCCATTT CGATACCTCG GGGACTTCCT TTGAATATAT

TCTGAGAGTA TGACAGTTGG TTTTCTTTCT TTCTTTCTAT

TGTTTTTGTT TTTATGGAAA TATAGCTTTG ATGATTTAGG

ATATTTTTTG TAGTGAACCA ATACATGCTT GATTAATATA

CGTACGAGGT GGGCATTCTA CTCTCATTAT TGGTGTTTTA

TTGGAGGAA AAATTAAATC TAGGAGTATC GTTTAGAGCG

CGAACGTAAT ATCCATGTTC TTCTCTTTGA AGAGGTCCCA

CCATTGCTTC CCAGATGCC AGCATTCTTC CATGATATTT

TGCGCTTGTT TTGCACTGGT GACACCCTTT CGAACCAAAG

ATGTCAAGTG CTGCTGATAC AACAACCTGT ATTCATACAA

TTCTGGATCC ATCAGCTCAC AATCCACAGC TGAAGATACA

GAAAATGATA CATGTCTCTG CAG
``` which codes the terminator sequence region of the endopolygalacturonase gene from *Kluyveromyces marxianus*. That expression cassette can be used in many different ways. The insertion cloning site is a cutting location at which the sequence can be cut open and the polynucleotide for the desired protein or peptide can be ligated in. In that simplest form after induction upon expression the protein is intracellularly produced and is not removed from the cell. It can then be obtained in per se known manner after opening the cell. This embodiment is suitable both for small peptides and proteins which are unstable outside the cell and also for proteins which are generally intracellularly located.

In a further embodiment which is suitable in particular for proteins which are to be removed from the cell, use is made of an expression and secretion system according to the invention. That system includes in operative association the nucleic acid sequence in accordance with SEQ ID No 1 or a part thereof which is active as a promoter, the sequence in accordance with SEQ ID No 2 as a terminator and, between those two sequences, the signal sequence in accordance with SEQ ID No 3

```
ATGT TATTCAGCAA CACCTTATTG ATCGCAGCAG CTAGTGCATT

ATTAGCTGAA GCTTCTCCAT TGGAAAAGAG A
``` for removal of the protein. In this embodiment culture is effected in per se known manner, wherein either in a continuous method the protein is continuously discharged into the medium and can be continuously obtained from the fermentation liquor or in a discontinuous method the cells are cultivated, harvested and then the protein can be obtained from the liquor.

The expression cassette according to the invention is suitable both for the expression of suitable autonomously replicating plasmids and also for incorporation in yeast chromosomes by way of integrative vectors.

Figure 1:
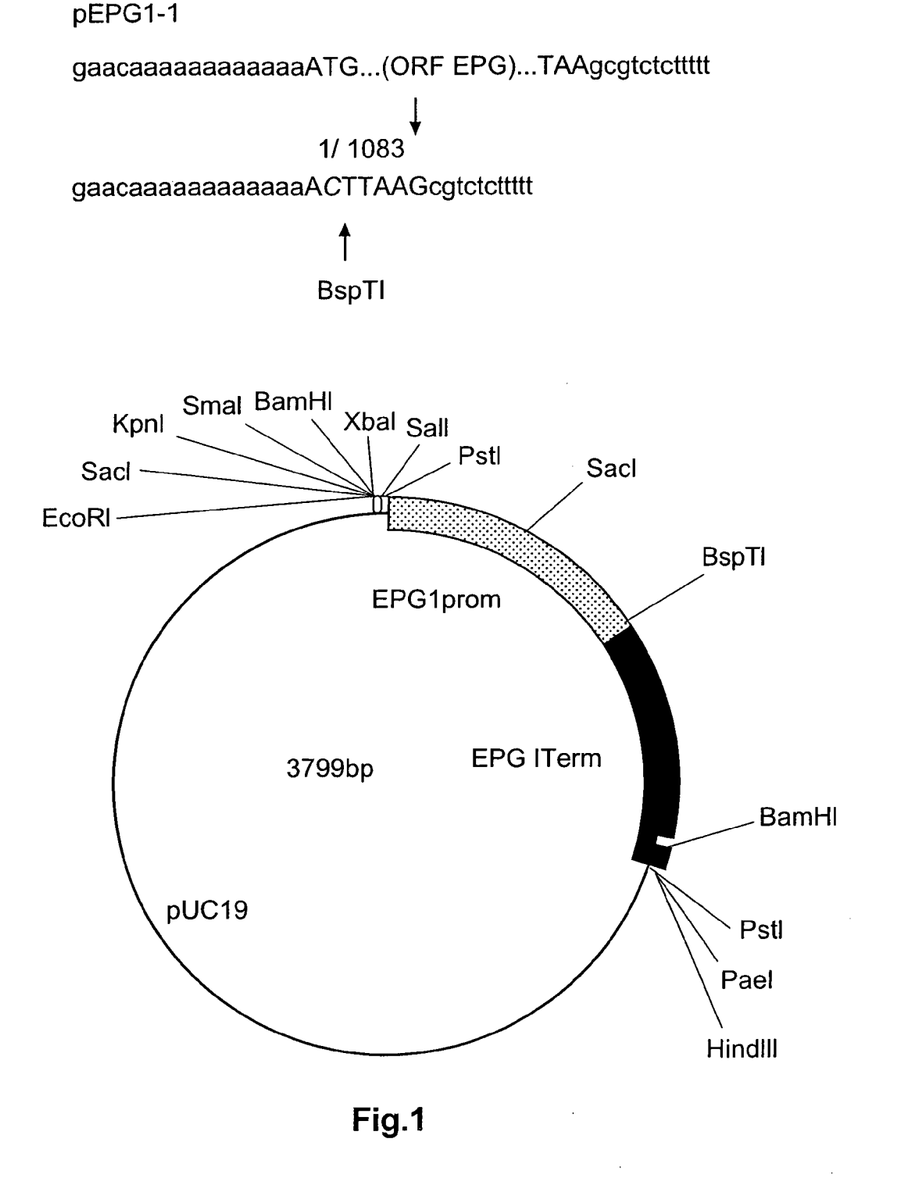
Figure 2:
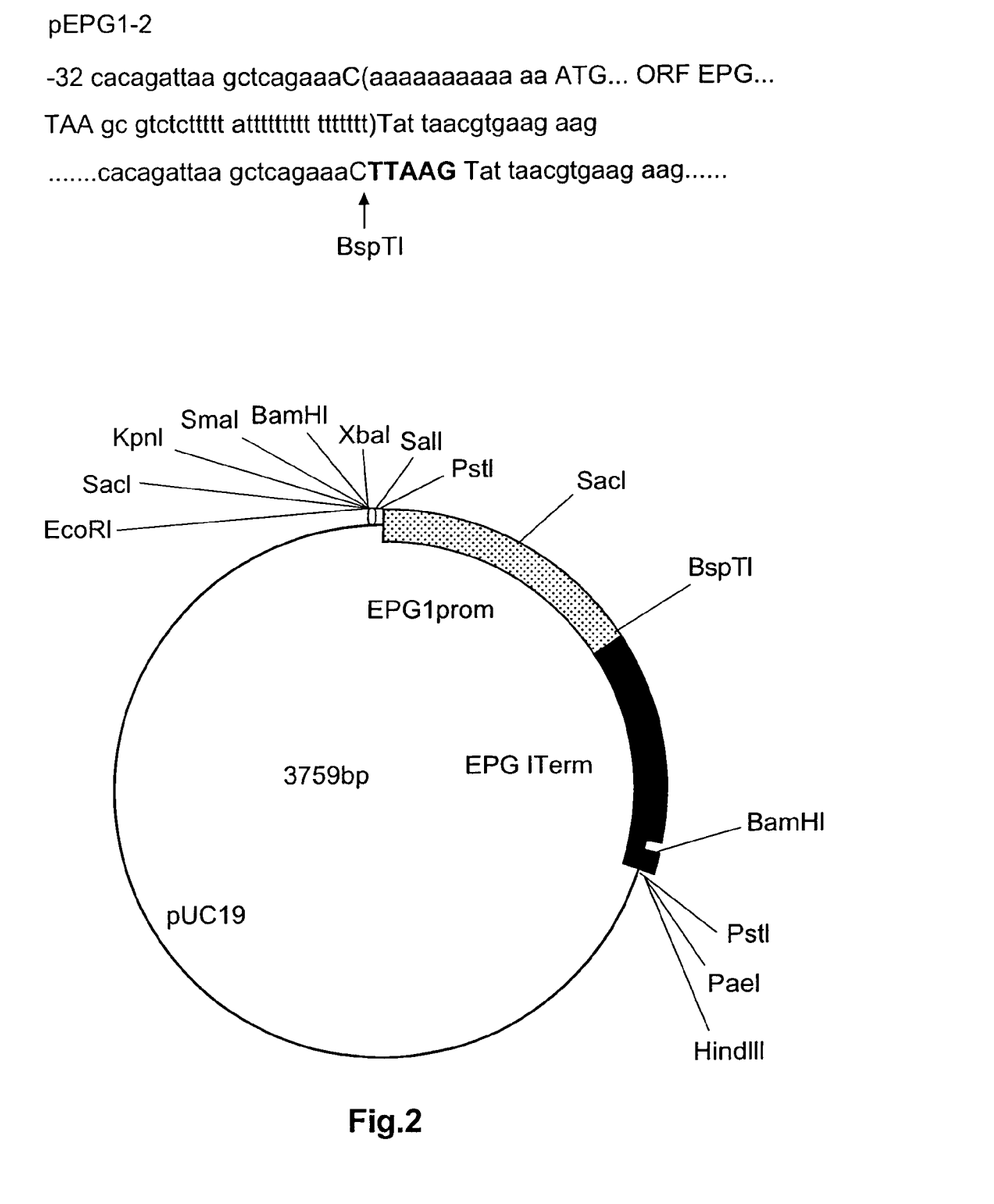
Figure 3:
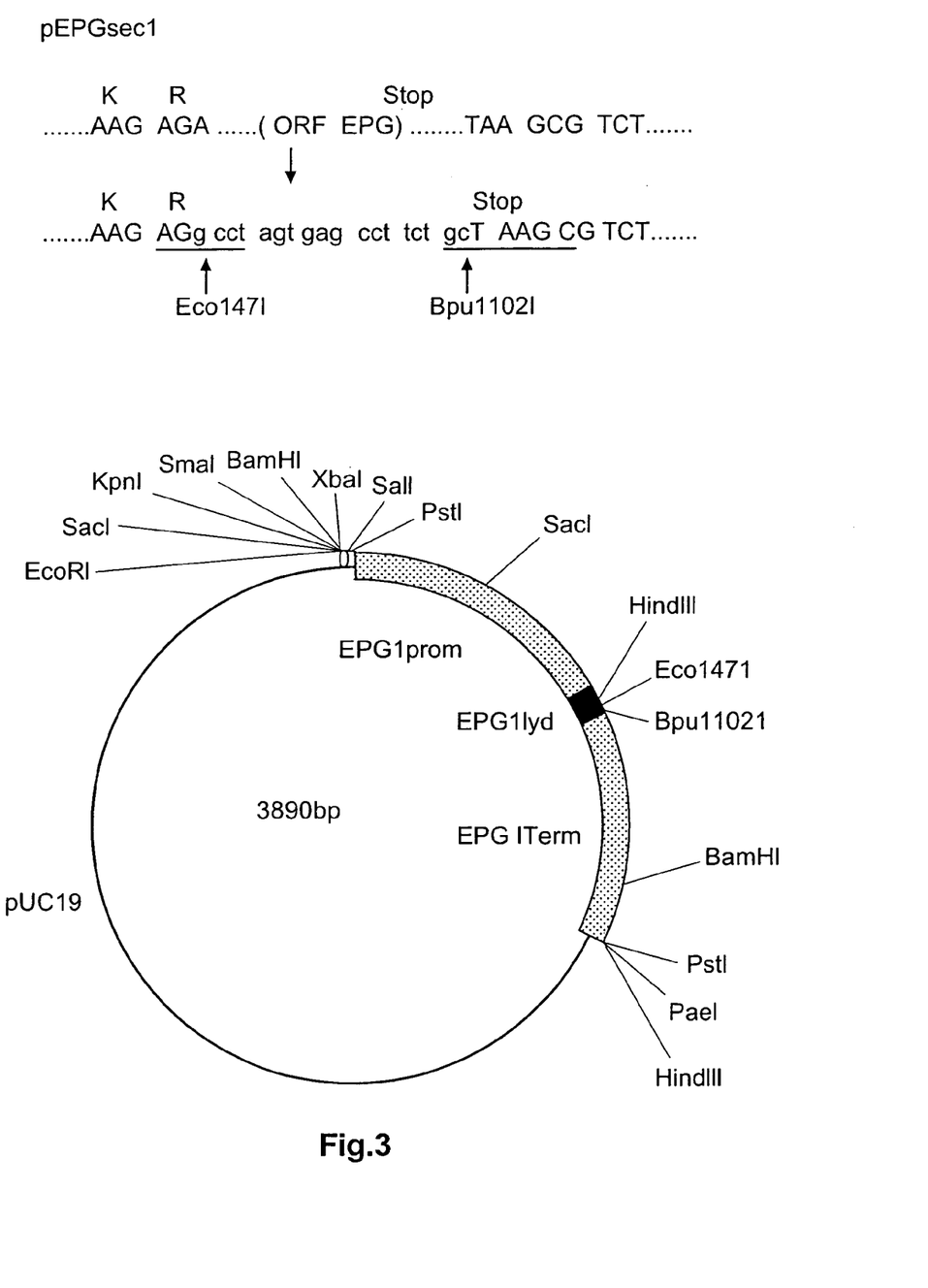

A further subject of the invention is the plasmids pEPG1-1, pEPG1-2 and pEPGsec which are described in greater detail with reference to FIGS. 1 to 3 and which contain the expression systems according to the invention. Those plasmids are recombinant bacterial plasmids and can be used in the present form for amplification of the expression cassettes. The plasmids are contained in the micro-organisms DSM 12919, DSM 12920, DSM 12921 or DSM 12922* and are deposited therewith [*Deposited on Jul. 13, 1999 at DSMZ, Mascheroder Weg 1b, 38124 Braunschweig].

It is however preferred for the plasmids, after the desired polynucleotide has been ligated in for the expression of a peptide or protein, to be amplified in *E. Coli*, then to obtain the plasmids, to cut out the expression cassette with suitable restriction endonucleases for which cut locations are provided at the edges of the expression cassette, and to ligate the expression cassette into a yeast vector. The vectors usually contain selection markers in order to be able to select successfully transformed cells in per se known manner.

The plasmids can possibly be multiplied in *E. Coli* and then put into *Kluyveromyces marxianus* or another *Kluyveromyces* strain or also another yeast strain. The transformation system used can be for example known plasmids based on the *Kluyveromyces drosophilarum* plasmid pKD1. Derivatives of that plasmid are suitable for use in *Kluyveromyces marxianus* and when using the expression system according to the invention result in effective expression and secretion of foreign proteins in the corresponding host.

In another embodiment it is possible for the expression cassette including the polynucleotide to be expressed to be cut out of the plasmids according to the invention, when prepared as above, and brought into contact as linear or circularised DNA-strand as an integration cassette directly with yeast cells in order to be absorbed thereby. By virtue of the homology with the endopolygalacturonase gene, then in a part of the treated cells, the DNA is received into the corresponding chromosome by exchange with the endogalacturonase gene. The selection of successfully transfected yeast cells is effected in this embodiment by way of the differing utilisation of pectin.

The expression cassette according to the invention is stably incorporated into chromosomes and, if the cells are cultured under optimum conditions, results in a good yield of the desired protein. The copy number of the system can be set in dependence on the nature of the peptide or protein to be expressed. As the endopolygalacturonase gene is only singly present in the chromosome set of the yeast, upon transfection or transformation with the expression system provided in accordance with the invention a copy of the expression vector is also present only for each successfully transformed cell. If a higher number of copies is desired, then sequences of a gene which is present in the chromosome set in a larger number of copies, for example for rDNA, is ligated in per se known manner to the ends of the expression cassette in order to cause a higher number of exchange events.

In the latter case a marker is additionally also incorporated in per se known manner into the sequence so that the successfully transformed cells can be selected. Methods and markers which are suitable for same are known to the man skilled in the art and do not need to be discussed in greater detail here.

The system according to the invention is highly variable. Thus for example only the sequence in accordance with SEQ ID No 1 or a part thereof which is active as a promoter can be combined with other nucleic acid sequences which provide further regulatory sequences and with a heterologous nucleotide sequence. The sequence in accordance with SEQ ID No 1 or a part thereof which is active as a promoter can be combined with the sequence of SEQ ID No 2 in order to provide a regulatory system which is homologous in *Kluyveromyces marxianus* and into which the polynucleotide for the protein to be expressed is inserted or it is possible for a system of SEQ ID No 1, SEQ ID No 2 and SEQ ID No 3 to be combined together with a gene to be expressed, which codes a desired protein, in order to produce a product which is to be discharged into the culture. As *Kluyveromyces* cells can be grown with many different C-sources and are not very demanding in respect of further nutrients and moreover are temperature-insensitive, this affords a highly effective system. Reliable expression of the foreign proteins is achieved by the regulatory sequence provided in accordance with the invention.

In accordance with the invention, there is provided a system which makes it possible to use the type of yeast *Kluyveromyces marxianus* which is highly promising as a host by virtue of its remarkable physiological capacities.

The system according to the invention is suitable for the expression of peptides, polypeptides, proteins and hybrid molecules including glycosylated proteins.

Thus in a further embodiment the expression cassette may also include the complete sequence of the endopolygalacturonase enzyme or parts thereof, wherein a sequence for a desired protein is ligated in between the endopolygalacturonase gene and the terminator sequence. Then, in this embodiment, upon expression, a hybrid is obtained, from which the endopolygalacturonase is separated in per se known manner.

Set out hereinafter are some definitions for terms which are used in the description.

Accordingly, an 'expression vector' is a DNA molecule which can be linear or of a ring shape and which contains a segment which codes a sequence for a protein or peptide which is of interest, which is operatively joined to regulatory sequences. Those regulatory sequences include at least promoter and terminator sequences. The expression vector can additionally contain selectable markers and further regulatory elements and must permit transmission and multiplication in host cells. Replication of the expression vectors can occur autonomously or by integration into the host genome.

The expression 'DNA' or 'polynucleotide' includes polymer forms of deoxyribonucleotides and ribonucleotides of any length and any modification in single- and double-stranded form.

The expression 'operatively joined' means that the individual segments are so arranged that they serve the intended purpose, that is to say they can inhibit transcription and can promote expression from the replication starting point to the termination sequence.

The claimed sequences may have further short sequences which do not interfere with the biological activity of the molecule. In addition the claimed sequences also include allele variants of the sequence, that is to say alternative forms of the gene which have occurred due to mutation.

The term 'protein or peptide' relates to a molecular chain of amino acids with biological activity. The proteins and/or polypeptides can be modified in vivo or in vitro, for example by glycosylation and phosphorylation. The term hybrid molecules is used to denote molecules which include both homologous parts and also heterologous parts, for example such proteins which include a combination of endopolygalacturonase or parts thereof with a foreign protein, or for example nucleotide sequences in which DNA from *Kluyveromyces marxianus* is combined with DNA from other micro-organisms.

The expression cassette according to the invention is suitable inter alia for yeasts of the strains *Kluyveromyces* and *Saccharomyces* and is preferably used in yeast strains of the type *Kluyveromyces marxianus* var. *marxianus*. A particularly preferred strain with particularly advantageous expression properties is *Kluyveromyces marxianus* var. *marxianus* BKM Y-719 which was described by Siekstele et al 1999 (Yeast 15, 311–322 1999)).

A further subject of the invention is a method of producing a recombinant protein which is characterised in that a yeast cell is transformed or transfected with an autonomously replicating plasmid which includes an expression cassette according to the invention and a polynucleotide which codes a foreign protein, the yeast cell is cultured under conditions which are suitable for the expression of the foreign protein, and the protein is obtained.

The subject of the invention is also a method of producing a recombinant protein which is characterised in that an expression cassette according to the invention is brought into a yeast cell where the expression cassette is incorporated into a chromosome, the cell is cultured and then the protein is obtained. Particularly preferably the expression cassette according to the invention is used as a module which permits the construction of episomal or integrative expression vectors which contain the regulatory sequences in accordance with SEQ ID No 1, No 2 and/or No 3.

The expression system according to the invention is suitable for the expression of various heterologous proteins. Particularly preferably the system is used for the expression of HBVS-antigen (hepatitis B virus, surface antigen) and virus protein 1 from polyoma virus. Those proteins are antigen proteins and can be particularly advantageously used as vaccines.

The invention is described by means of the accompanying Figures and the following Examples.

FIGS. 1 to 4 show plasmids with the expression cassettes according to the invention and FIG. 6 shows the primers used in Example 2.

FIG. 1 shows the plasmid pEPG1-1. That plasmid includes an expression cassette with the promoter according to the invention in accordance with SEQ ID No 1 (referred to as EPG1prom), an insertion cloning site which can be cut with BspT1, and the terminator sequence according to the invention in accordance with SEQ ID No 2 (referred to as EPG1term). That expression cassette was ligated into the multicloning site of the plasmid pUC19. The insertion cloning site which can be cut with BspT1 replaces the open reading frame of the endopolygalacturonase gene which was removed.

FIG. 2 shows the plasmid pEPG1-2. That plasmid contains the expression cassette according to the invention, which includes a sequence in accordance with SEQ ID No 1 with the nucleotides 572 to 1134 (referred to as EPG1prom) which is active as a promoter, an insertion cloning site which can be cut with BspT1, and a terminator sequence which includes the nucleotides 28 to 541 of SEQ ID No 2 (referred to as EPG1term). The insertion cloning site replaces the open reading frame of the endopolygalacturonase gene inclusive of the sequences −1 to −12 and 1087 to 1115 of that gene.

FIG. 3 shows the plasmid pEPGsec. That plasmid contains an expression and secretion system of the invention. The plasmid contains an expression cassette with a promoter in accordance with SEQ ID No 1 (referred to as EPG1prom), a terminator in accordance with SEQ ID No 2 (referred to as EPG1term), a signal sequence in accordance with SEQ ID No 3 (referred to as EOG1lyd) and two cut locations in order to insert the desired nucleic acid sequence for the protein to be expressed. That expression cassette was ligated into the multicloning site of the plasmid pUC19. The open reading frame of the endopolygalacturonase gene was removed from positions 75 to 1084 and replaced by a linker with the cloning sites Eco 1471 and BpU 11021.

FIG. 4 shows the plasmid pUC19PG. A 2.198 kb PstI-DNA-restriction fragment from a recombinant lambda GEM™-12-bacteriophage of a genomic gene bank of *Kluyveromyces marxianus* was ligated into the PstI-restriction location of the multicloning site of the plasmid pUC19.

FIG. 5 shows the plasmid pUC19-PG1a. A 2.735 kb StuI-PvuII-DNA-restriction fragment from a recombinant lambda GEM™-12-bacteriophage of a genomic gene bank of *Kluyveromyces marxianus* was exchanged in the plasmid pUC19 for the 321 kb fragment. The bold part of the plasmid corresponds to the DNA fragment from *K. marxianus* while the thin-printed part represents the proportion of the plasmid pUC19.

Four micro-organisms which contain the plasmids in accordance with FIG. 1, FIG. 2, FIG. 3 and FIG. 4 were deposited at the DSMZ in accordance with the requirements of the Budapest Treaty. *E. coli* pEPG1-1 is deposited under deposit number DSM 12919, *E. coli* pUC19PG is deposited as DSM 12920, *E. coli* pEPGseq deposited under the number DSM 12921 and *E. coli* pEPG1-2 under the deposit number DSM 12922.

EXAMPLE 1

Figure 4:
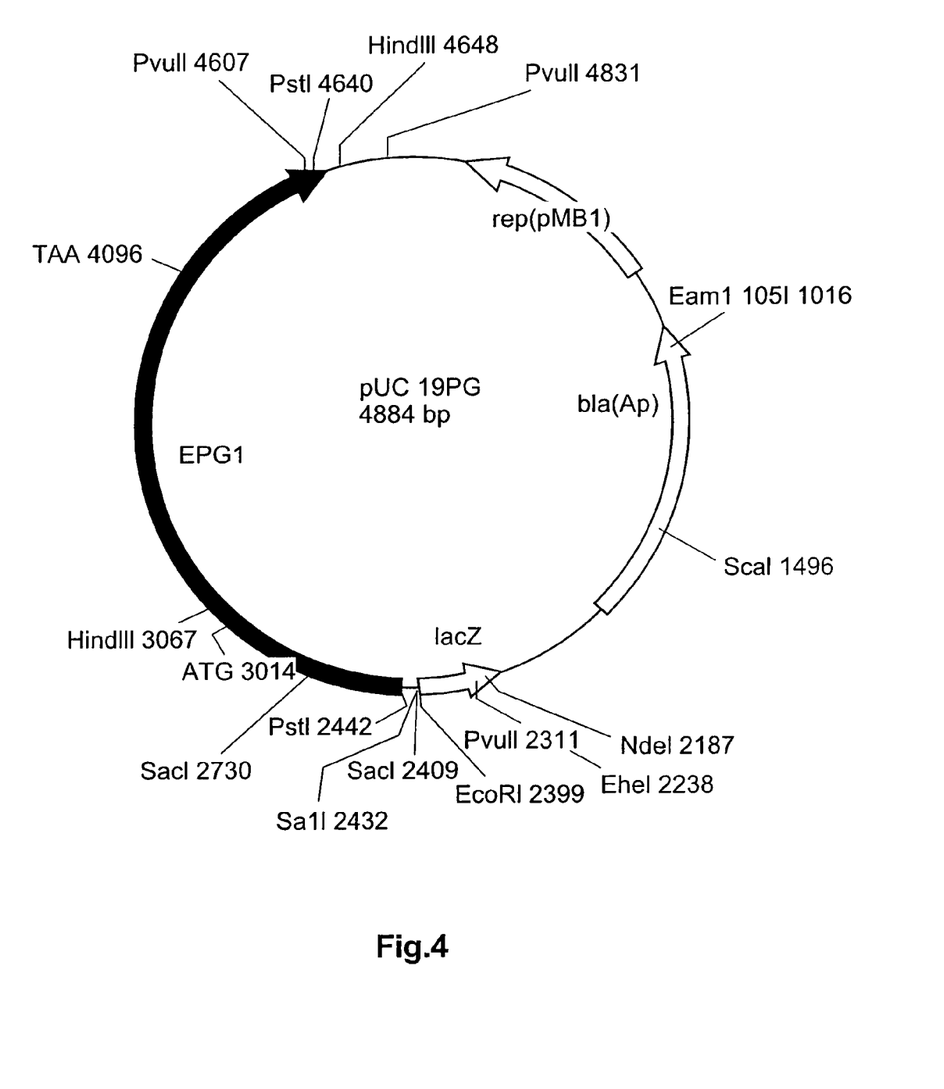

Manufacture of the Basic Plasmid for the Production of the Expression Casssettes A Pst1-DNA-fragment with 2.198 kb, which contains the complete gene of the endopolygalacturonase (EPG1) with the regulatory sequences was inserted into the PstI-cut location of the multicloning site of the bacterial plasmid pUC19. That construct is shown in FIG. 4. Using in each case two opposite primers which at the 5'-end bore a recognition site for the restriction enzyme BstT1 and at the 3'-end have homology with the promoter, signal and/or terminator sequence of the EPG1-gene, it was possible by means of PCR passing around the plasmid to produce a DNA fragment which after restriction with BspT1 could be circularised with a ligase. When using different recognition sites for restriction enzymes at the 5'-ends of the PCR primers, suitable linkers had to be ligated in for circularisation ligation or the primers contained additional sequences at the 5'-end, which represented a common recognition site for the restriction enzyme. Depending on the respective choice of primers, defined areas of the EPG1 region can be deleted from the plasmid by restriction and subsequent circularisation. The recombinant deletion plasmids were amplified in *Escherichia coli* and served as a basis for the expression cassettes. By way of the various recognition sites for restriction enzymes in the multicloning site of the plasmid pUC19 the cassette can then be cut out and cloned into an episomal or integrative vector for a suitable yeast strain. The cassette can also be used directly as a PstI-DNA-fragment for integration into a yeast host strain.

EXAMPLE 2

Manufacture of a Recombinant Plasmid with Sequence ID No 1, No 2 and No 3

Figure 5:
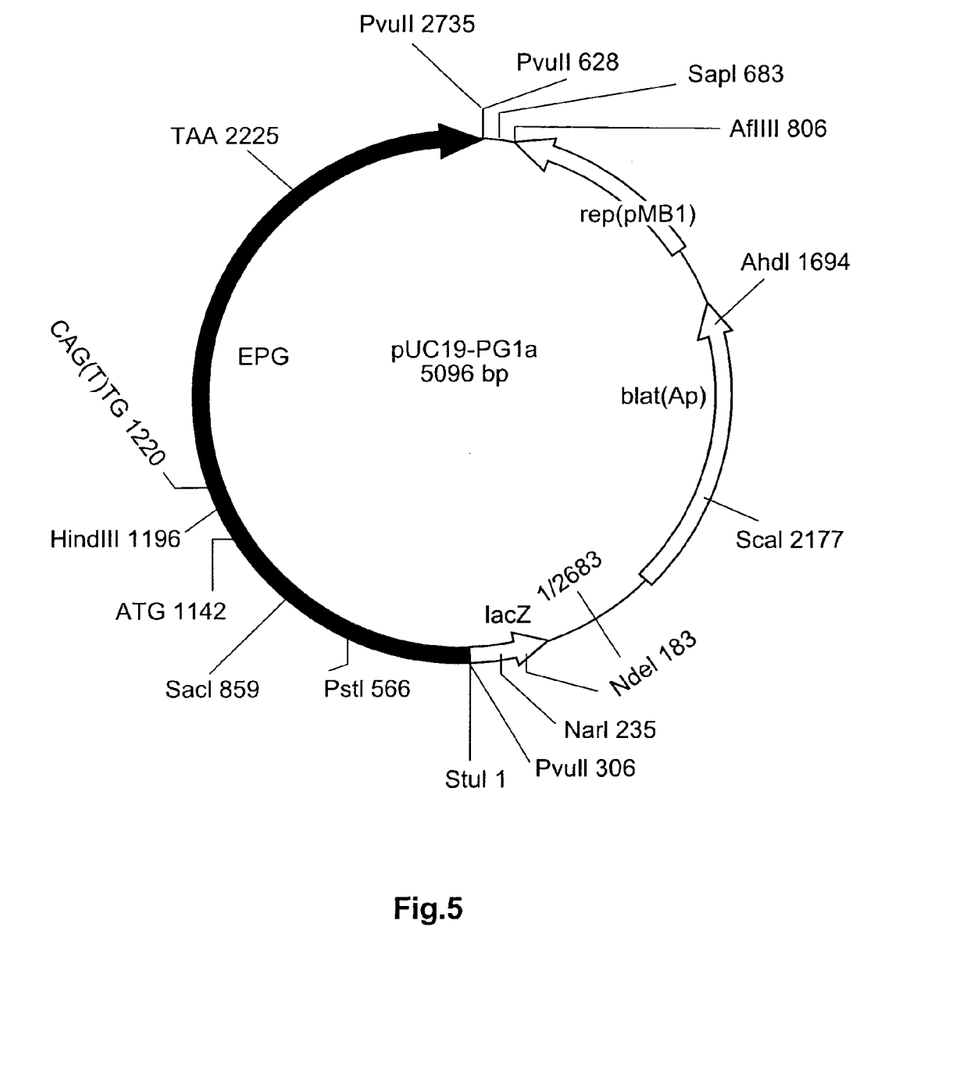

In the bacterial basic plasmid pUC19 the 321 bp PvuII fragment was replaced by a StuI/PvuII DNA fragment of 2.735 kb which contains the complete endopolygalacturonase gene inclusive of the regulatory sequences −1142 to −1 and +1087 to 1595 from *Kluyveromyces marxianus*. The StuI/PvuII fragment was for that purpose isolated from a recombinant lambda GEM™-12-bacteriophage of a genomic gene bank of *Kluyveromyces marxianus*. A map of the plasmid produced: 'pUC19-PG1a' is shown in FIG. 5. That plasmid can be used in a similar manner to Example 1 for the production of expression cassettes. As the multicloning site was completely deleted by the cloning strategy with that plasmid and the StuI location in the upstream promoter region of the EPG1 gene was destroyed by ligation with the PvuII location in the pUC19, the PvuII site which has remained downstream in relation to the EPG1 gene and for example the unique NarI site in the lacZ-part of the pUC19 can be used for cutting out the cassette.

Figure 6:
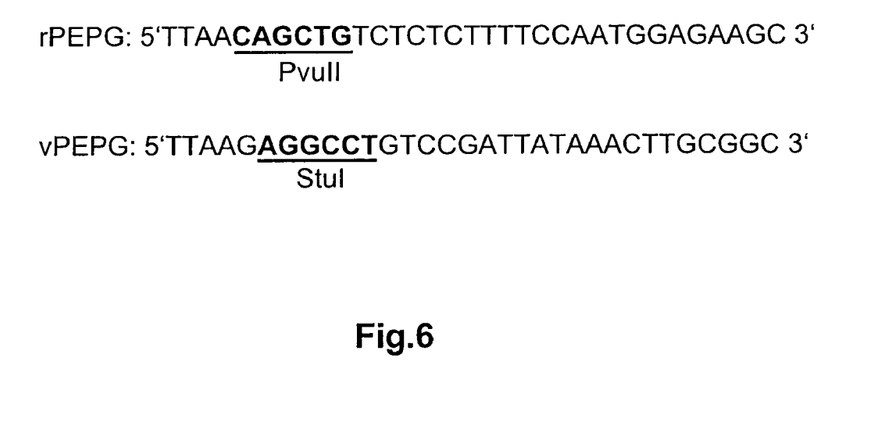
FIG. 6 shows the primers in accordance with SEQ ID Nos 4 and 5, which are used for the cloning of promoter and signal sequence.
Figure 7:
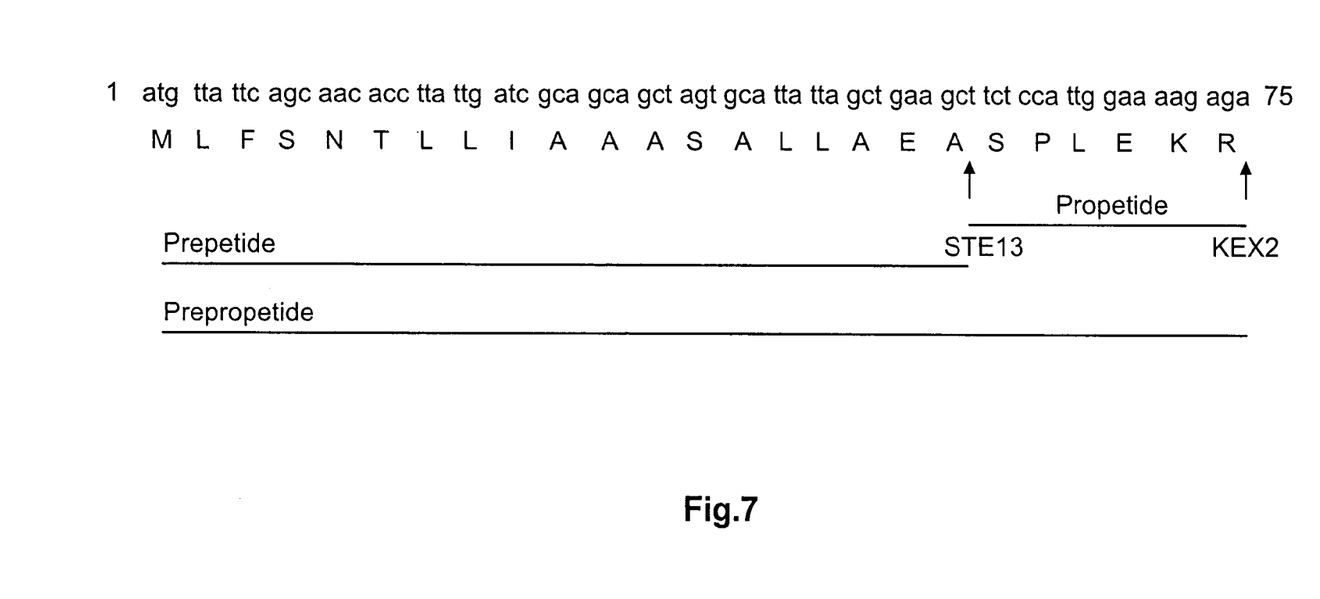
FIG. 7 shows the signal sequence in accordance with SEQ ID No 3 and the associated signal peptide (with sequence for pre- and prepropeptide) of the endopolygalacturonase from *Kluyveromyces marxianus*.

By means of the PCR and using the primers shown in FIG. 6 (SEQ ID No 4 and No 5) it is possible to generate a DNA fragment which contains the promoter region and the signal sequence in accordance with SEQ ID No 1 and No 3. The degenerated rPEPG primer has in the 5' region a mismatch with respect to the EPG1 sequence in the region 1220 and thereby generates from the EPG1 sequence: CAGTTG a PvuII site (CAGGTG). That point mutation (transition) leads to an amino acid exchange insofar as a cysteine codon is changed from TGT into an arginine codon after CGT. That exchange occurs however in the proportion of the endopolygalacturonase which is replaced by the reading frame of a foreign gene and therefore has no influence on the expression. The StuI/PvuII-PCR fragment can be inserted as a blunt end into the multicloning site of a corresponding vector. By way of the PvuII site it is possible 'in frame' to add open reading frames of genes whose expression product is to be removed from the cell.

EXAMPLE 3

Manufacture of Polyoma JCV Major Coat Protein VP1:

For the expression of the JCV VP1-gene the expression cassette pEPG1-1 was used. The VP1 gene was amplified by means of PCR using the primers:

JC5 (SEQ ID No 6): 5'TCAAGCTTAAGAATGGC-CCCAACAAAAAGA 3' and

JC3 (SEQ ID No 7): 5'GTAAGCTTAAGATTACAG-CATTTTTGTCTG 3' and cloned as a BspT1 fragment into the expression cassette of pEPG1-1. The cassette was cleaved with Pst1 and the DNA fragments were converted at their ends by means of T4 polymerase to blunt ends.

The 'blunt ended' cassette was inserted into the Sma1 site of the *Kluyveromyces* vector pKDSU. The transcription direction of the VP1-gene is in that case opposite to transcription of the S. cerevisiae URA3 gene.

The recipient (BKM Y-719 ura) was transformed with the expression construct and uracil prototrophic clones were isolated. The presence of the expression cassette with the reading frame of the VP1 gene was checked by means of PCR and the above-indicated primers. Selected clones were cultivated in various liquid media. The yeast cells were harvested by centrifuging and broken up in lysis buffer (10 mM TRIS-HCl, pH 7.5, 0.01% TRITON×100, 1 mM $CaCl_2$, 100 mM NaCl with 1 mM PMSF) with micro-glass beads at 0° C. The glass beads were then sedimented by centrifuging (2000 rpm) for 10 minutes. The supernatant material was arranged in a layer on a 20% saccharose pad (in lysis buffer) and centrifuged for 2 hours at 4° C. and 35,000 rpm (Beckman L8-75 rotor SW41). The pellet was suspended in lysis buffer and arranged in a layer on a CsCl-gradient (1.24 to 1.38 g/ml CsCl). The centrifuging operation was effected at 4° C., 35,000 rpm for 16 hours in the SW41 rotor. 'Virus like particles' of the JCV VP1 of an average particle size of 45 nm were obtained from the fractions between 1.3 and 1.34 g/ml CsCl.

EXAMPLE 4

Manufacture of Hepatitis B Virus Surface Antigen (HBV s-Antigen):

The expression cassettes pEPG1-1 and pEPG1-2 were used for expression of the HBV s-antigen gene of subtype (AYW). The HBS gene was amplified by means of PCR using the primers:

HB5 (SEQ ID No 8): 5'AGCCTTAAGATAATGGAGAA-CATCACATCAGG 3' and

HB3 SEQ ID No 9): 5'TGACTTAAGTTAAATGTATAC-CCAAAG 3' and cloned as BspT1 fragment into the expression cassettes. The cassettes were cleaved with BamH1 and the DNA fragments filled at their ends by means of Klenow polymerase to form blunt ends.

The 'blunt ended' expression cassettes were inserted into the Sma1 site of the *Kluyveromyces* vector pKDSU. The transcription direction of the HBS gene in that case is opposite to the transcription of the S. cerevisiae URA3 gene. The recipient (BKM Y-719 ura) was transformed with the expression constructs and uracil prototrophic clones were isolated on selective medium. Whole DNA was isolated from selected clones and used for detection of the expression cassette by means of PCR. Positive clones were cultivated in liquid, synthetic and in complete media and used for the production of S-protein particles. Corresponding yeast cultures were harvested by centrifuging and broken up in a PBS buffer with 1 mM PMSF with micro-glass beads at 0° C. The glass beads were then sedimented by centrifuging (2000 rpm) for 10 minutes. The yeast membrane fraction was sedimented from the supernatant material by centrifuging for 30 minutes at 14,000 rpm (J20 Rotor Beckman J2-21). HBV s-antigen sedimented with that fraction and was eluated by 0.5% Tween-20 in PBS from the fraction. After renewed centrifuging at 14,000 rpm the supernatant material was obtained and separated off by CsCl-density gradient centrifuging. Highly purified HBV s-antigen particles were isolated from the 1.2 g/ml CsCl fraction.

The yield of isolatable antigen, in cultivation in synthetic media, with the pEPG1-2 cassette, was twice as high as with the pEPG1-1 cassette.

---

The invention claimed is:

1. An isolated nucleic acid including the nucleotide sequence of SEQ ID No: 1.

2. A yeast expression cassette comprising in operative junction the nucleotide sequence of SEQ ID No 1, nucleotides 1–1134 of SEQ ID NO: 1 or a part of nucleotides 1–1134 of SEQ ID NO: 1 that comprises nucleotides 572–1134 of SEQ ID NO: 1, which is active as a promoter, an insertion cloning site and the nucleotide sequence of SEQ ID No 2 or a part thereof of SEQ ID NO: 2 that comprises nucleotides 28–541 of SEQ ID NO: 2, which is active as a terminator.

3. A yeast expression and secretion cassette comprising in operative junction the nucleotide sequence of SEQ ID No 1, nucleotides 1–1134 of SEQ ID NO: 1 or a part of nucleotides 1–1134 of SEQ ID NO: 1 that comprises nucleotides 572–1134 of SEQ ID NO: 1, which is active as a promoter, the nucleotide sequence of SEQ ID No 3, an insertion cloning site and the nucleotide sequence of SEQ ID No 2 or a part of SEQ ID NO: 2 that comprises nucleotides 28–541 of SEQ ID NO: 2, which is active as a terminator.

4. Plasmid pEPG1-1 containing a yeast expression cassette according to claim 2 deposited under the deposit number DSM 12919.

5. Plasmid pEPG1-2 containing a yeast expression cassette according to claim 2 deposited under the deposit number DSM 12922.

6. Plasmid pUC19PG deposited under the deposit number DSM 12920.

7. Plasmid pEPG sec containing a yeast expression cassette according to claim 3 deposited under the deposit number DSM 12921.

8. An expression vector containing in operative junction a promoter with the sequence of SEQ ID No 1, the sequence of nucleotides 1–1134 of SEQ ID NO; 1 or apart of the sequence of nucleotides 1–1134 of SEQ ID NO: 1 that comprises nucleotides 572–1134 of SEQ ID NO: 1, which is active as a promoter, a polynucleotide which encodes a heterologous protein, and the nucleotide sequence of SEQ ID No 2 or a part of SEQ ID NO: 2 that comprises nucleotides 28–541 of SEQ ID NO: 2, which is active as a terminator.

9. An expression vector according to claim 8 which in addition also includes a signal sequence between promoter and polynucleotide.

10. An expression vector according to claim 9 wherein the signal sequence is a sequence in accordance with SEQ ID No 3.

11. An expression vector according to one of claims 8 to 10 wherein the polynucleotide encodes an antigen protein or peptide.

12. An expression vector according to claim 11 wherein the polynucleotide codes a hepatitis B surface antigen, VP1 from polyoma virus or protein A from *Staphylococcus*.

13. An expression vector according to one of claims 8 to 10 wherein the vector is an integrative or episomal vector.

14. An expression vector according to one of claims 8 to 10 wherein the vector is a plasmid replicatable in yeast.

15. A host cell that has been transformed with an expression vector or a plasmid according to one of the preceding claims.

16. A host cell according to claim 14 wherein it is a cell of the type *Kluyveromyces marxianus*.

17. *E. coli* pEPG1-1 deposited under the deposit number DSM 12919.

18. *E. coli* pUC19PG deposited under the deposit number DSM 12920.

19. *E. coli* pEPG see deposited under the deposit number DSM 12921.

20. *E. coli* pEPG1-2 deposited under the deposit number DSM 12922.

21. A method of manufacturing a recombinant protein, wherein a yeast cell is transfected or transformed with a plasmid which includes the expression cassette according to one of claims 2 and 3 and a polynucleotide which encodes a heterologous protein, the yeast cell is cultured under conditions which are suitable for the expression of the foreign protein, and the protein is produced.

22. A method of manufacturing a recombinant protein wherein an expression cassette according to claim 2 or claim 3 is put into a yeast cell where the expression cassette is incorporated into a chromosome, the cell is cultured and then the protein is obtained.

* * * * *